United States Patent [19]

Buchalter

[11] 4,058,127
[45] Nov. 15, 1977

[54] METHOD OF APPLYING VISCOUS FLUID TO A SURFACE

[76] Inventor: Gilbert Buchalter, 555 Mount Prospect Ave., Newark, N.J. 07104

[21] Appl. No.: 681,074

[22] Filed: Apr. 28, 1976

Related U.S. Application Data

[62] Division of Ser. No. 416,230, Nov. 15, 1973, Pat. No. 4,002,239.

[51] Int. Cl.² ............................................. A61N 1/04
[52] U.S. Cl. ............................. 128/417; 128/419 D
[58] Field of Search ............. 128/417, 419 D, 2.06 E, 128/2.1 E, 404, 405, 410, 411, 416, 418, DIG. 4; 229/43

[56] References Cited

U.S. PATENT DOCUMENTS

| | | | |
|---|---|---|---|
| 3,048,549 | 8/1962 | Adams | 128/DIG. X |
| 3,151,619 | 10/1964 | Sullivan | 128/417 |
| 3,340,868 | 9/1967 | Darling | 128/2.06 E |
| 3,467,863 | 9/1969 | Karsh | 128/419 D X |
| 3,487,827 | 1/1970 | Edmark | 128/2.06 E |
| 3,498,525 | 3/1970 | Zinkgraf | 229/43 |
| 3,702,613 | 11/1972 | Panico et al. | 128/417 |

*Primary Examiner*—Dalton L. Truluck
*Assistant Examiner*—Lee S. Cohen
*Attorney, Agent, or Firm*—Lerner, David, Littenberg & Samuel

[57] ABSTRACT

A cardiac defibrillator cup is provided which can be designed to hold a unit dose of electrolytic gel, and is adapted to be applied and adhered to defibrillator paddles or electrodes, and thus, serve as an immediate source of gel therefor. The cup comprises a flexible container for holding gel, said container having an open face; the peripheral edges of said open face and/or area surrounding said open face includes a bonding agent for removably adhering the cup to a defibrillator paddle. Prior to application to such paddle, the open face of the cup will be closed off by a protective cover, which cover is removably secured to said bonding agent.

2 Claims, 4 Drawing Figures

METHOD OF APPLYING VISCOUS FLUID TO A SURFACE

This is a division of application Ser. No. 416,230, filed Nov. 15, 1973, now U.S. Pat. No. 4,002,239, issued Jan. 11, 1977.

FIELD OF THE INVENTION

The present invention relates to a container for holding a semi-solid or even a liquid, and particularly relates to a cardiac defibrillator cup which holds an electrolyte, such as gel, and is adapted to be secured directly to the paddles or electrodes of a cardiac defibrillator apparatus.

BACKGROUND OF THE INVENTION

Fibrillation is a medical term for describing the sequence of events wherein the rhythm of the heart muscle breaks down and muscle tissue contracts incoordinately and uncontrollably. Immediate treatment is required to control such arrhythmia and bring the heart muscle back to its normal rhythm. If the required treatment is delayed, for even seconds, the result may be failure and death of the patient.

A number of treatments are indicated to correct heart fibrillation. One such treatment is drug therapy. A more direct and faster-acting treatment is the application of very high voltages to areas of the heart muscle for short periods. The latter treatment is normally carried out employing external defibrillator apparatus. Such apparatus includes a pair of electrodes or paddles, hereinafter referred to as electrode paddles or paddles, having a flat or convex surface, which are designed to be placed in direct contact with the patient's body. Electrical impulses are then applied to the patient through the electrode paddles.

Before the electrode paddles can be applied to the patient's skin, the paddles must be covered with an electrically conductive preparation so that the bare metal forming the paddles does not directly contact the skin. If the paddles are used without a covering, or with an insufficient covering, they can produce severe burning with resulting blistering of the skin which in turn may lead to infection.

In order to overcome the afore-described problem, the paddles are usually employed in conjunction with an electrically conductive liquid, cream or gel which serves to facilitate the transfer of electrical impulses from the electrodes to the patient. The electrolyte is applied to the paddles or to the body of the patient, then the electrode paddles are pressed against the body maintaining firm contact during the operation of the defibrillator.

In applying the electrolyte to the patient's body, the electrolyte is usually dispensed from a container onto a piece of cotton which is then rubbed over the area of the patient's skin to be grounded. Alternatively, the electrolyte may be dispensed directly from a container, such as a tube or even an aerosol package, onto the paddles or the patient's skin and distributed over the desired area.

The above procedure for applying electrolyte to the patient's skin is a relatively time consuming operation when time is clearly of the essence and seconds are critical. If for some reason, the container of electrolyte is not readily available, for example, it is misplaced or empty the result could be loss of life. Further, the electrolyte, which preferably is in the form of a pasty lotion or gel, may gum-up and cause clogging of the container, especially where the cap of the container is not immediately replaced after use, preventing dispensing thereof at the needed time. Such an occurrence, could be fatal.

If an aerosol container is employed, should the aerosol valve become inoperative, which can be a frequent occurrence, the time lost in locating another source of electrolyte could mean irreparable damage to the patient. Furthermore, should an insufficient amount of such electrolyte be distributed on the patient's skin, the high voltages administered can cause severe burning of the patient, possibly ineffective treatment and loss of life.

BRIEF DESCRIPTION OF THE INVENTION

In accordance with the present invention, there is provided a container or cup which holds electrolyte, such as a gel, and is especially adapted for use in conjunction with cardiac defibrillator apparatus, as well as with other apparatus for use in administering electrical impulses to a patient, such as electro-shock equipment. Such cup provides a ready source of electrolyte and may be employed for administering electrolyte to the patient's body in such manner, as will be hereinafter described, to overcome the disadvantages inherent with use of the prior art techniques described above. The cardiac defibrillator cup of the invention is adapted for one time use and is easily disposed of thereafter.

SUMMARY OF THE INVENTION

The cardiac defibrillator cup in accordance with the invention comprises a flexible container adapted to hold a liquid or semi-solid or gelled electrolyte, said container having an open face, the peripheral edges defining said open face having a bonding agent disposed thereon adapted to removably secure said container to a substantially flat surface, such as the surface of conventional electrode paddles employed with external defibrillator apparatus. The cardiac defibrillator cup of the invention including the contents thereof, is preferably secured to electrode paddles and stored thereon. Thus, when an emergency arises and the paddles must be quickly used, the operator need not first apply electrolyte to the skin of a patient at the expense of loss of precious time as described above; all the operator need do is squeeze the contents of the cup secured to the paddle onto the paddle, and apply the paddle on the patient's skin.

The cardiac defibrillator cup of the invention includes a protective cover which is removably secured to the open face of the container by means of said bonding agent, to thereby close off the contents of the cup to the atmosphere before the cup is secured to the surface of an electrode paddle. The protective cover is removed from the container immediately prior to securing the container to the electrode paddle.

Thus, it is seen that the bonding agent disposed on the peripheral edges defining the open face of said container performs dual functions, namely, removably securing the protective cover to the container to close off the contents thereof and after the protective cover is removed, removably securing the cup with its contents to the electrode paddle.

In a preferred embodiment of the invention, the peripheral edges defining the open face of the container also define a flat lip which extends outwardly away from the open face. The lip provides an area on which the bonding agent is disposed as well as a good contact area for securely bonding the protective cover to the container and for bonding the container to the electrode paddle.

Further, in the preferred embodiment of the cardiac defibrillator cup of the invention, the container will include depressions to facilitate grasping of the container and squeezing thereof just by the use of the fingers to dispense the contents thereof. The container itself will preferably be of a pyramidal shape having at least three or four or more sides, preferably three sides, with the open face thereof defining the base. It will also be understood that the container, in other embodiments, may be cylindrical, spherical, multisided or accordian in shape or design. In addition, the container may have rounded sides or may be in the form of a pouch or bag.

DETAILED DESCRIPTION OF THE INVENTION

Figure 1:
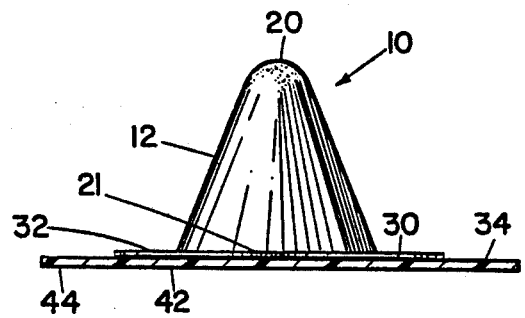
FIG. 1 is a side elevational view of a preferred embodiment of the cardiac defibrillator cup of the invention.
Figure 2:
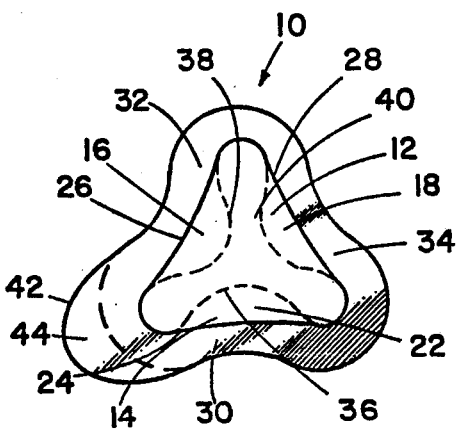
FIG. 2 is a bottom view of the cup of FIG. 1.
Figure 3:
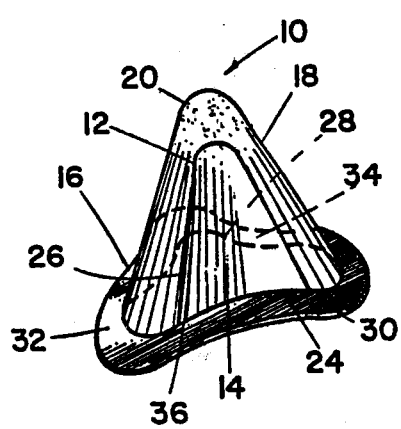
FIG. 3 is a perspective view of the cup of FIG. 1.

Referring to the accompanying Figures, wherein like parts are represented by like numerals in the several views, in FIGS. 1, 2 and 3 there is shown a preferred embodiment of the cardiac defibrillator cup of the invention represented by the numeral 10. The cup 10 includes a container portion 12, of substantially pyramidal shape, defined by the walls 14, 16 and 18 which extend from the apex 20 to the base 21 which comprises an open face 22 defined by the peripheral edges 24, 26 and 28.

As shown, the peripheral edges 24, 26 and 28 terminate in outwardly extending flat lip 30, 32 and 34, respectively.

The walls 14, 16, and 18 include depressions 36, 38 and 40, respectively, (partially shown in FIG. 3 and indicated by the broken lines in FIG. 2) to facilitate grasping of the container and squeezing said walls to empty the contents thereof.

The lip 30, 32, and 34 is provided with bonding agent and positioned over said lip is protective cover 42 (shown in FIGS. 1 and 2 and which usually will be formed of transparent plastic sheet) and is removably secured to said lip via said bonding agent. The protective cover 42 includes tab 44, which may comprise a portion of said cover extending beyond the lip as shown, for facilitating removal of said cover from container 12, to expose the contents thereof.

The afore-described cardiac defibrillator cup is employed as follows. The protective cover 42 is removed by grasping tab 44 and lifting it up and away from the lip 30, 32 and 34. The bonding agent will remain on the exterior or bottom surface of the lip. The container 12 is then pressed against a surface 46 of an electrode paddle 48 (shown in FIG. 4) so that the exterior or bottom surface of the lip 30, 32 and 34 which has bonding agent disposed thereon contacts the paddle and is firmly, yet removably, bonded thereto. Of course, each of the paddles of the defibrillator apparatus will have a defibrillator cup attached thereto.

Figure 4:
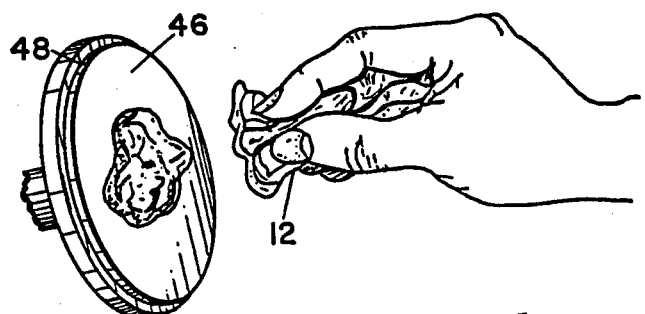
FIG. 4 is a view of the cup of FIG. 1 as employed for applying a gel electrolyte to the flat surface of an electrode paddle.

When an emergency arises necessitating use of the defibrillator apparatus, the operator grips and squeezes walls 14, 16, and 18 of container 12 with his thumb and fingers thereby expelling electrolyte out of the container 12 and onto the surface 46 of the electrode paddle 48 as shown in FIG. 4. During this operation, the cup 10 is forced from the surface of the paddle. The electrolyte gel is distributed over the surface 46 of paddle 48 using the empty cup as a spatula or the paddle is applied with a circular motion which motion uniformly distributes the gel to the skin of the patient.

Use of the afore-described cup and technique avoids all of the pitfalls inherent in prior art techniques for applying electrolyte. Perhaps the main advantage of the invention is that it provides a source of electrolyte which is already in place on the electrode paddle, ready for use at an instant's notice.

It will be appreciated that the container portion of the cup of the invention can take any convenient form such as the forms described above as well as a cone-form, spherical form, square form, rectangular form and the like. Regardless of the form employed, the container will include the one open face and the peripheral edges defining said open face will extend out to form a lip as described. The open face thereof can be of any desired size including large enough to cover the entire area of the electrode paddle.

The container itself will be adapted to hold any desired amount of electrolyte and preferably a unit dose thereof.

The container itself will preferably be of one piece flexible construction. Examples of materials suitable for use in forming the container include plastics such as polyvinyl chloride, polyethylene, polypropylene, butyrates, propionates, and other flexible or semi-flexible materials, including rubber, metal, paper or combinations. A preferred container material is polyvinyl chloride.

The container can be formed by conventional molding or forming processes.

The bonding agent disposed on the lip of the container must be such that it will removably bond the protective cover to the lip of the container so that a sufficient portion of the bonding agent will remain on the lip even after the protective cover is removed from the container, so that the container can be bonded to the electrode paddle. Suitable bonding agents which can be employed herein include any conventional pressure-sensitive adhesives, as will be apparent to one skilled in the art.

The protective cover is preferably formed of a sheet material which is adapted to be removably secured to the bonding agent disposed on the lip of the container, so that when the protective cover is removed from the container, it will not pull off all or even a substantial portion of the bonding agent with it. Examples of suitable sheet materials which can be employed as protective covers include plastic sheeting such as polyethylene and other conventional release films, foils and treated papers.

The electrolytes which may be employed in the cardiac defibrillator cup of the invention can comprise any conventional electrode gel, jelly, liquid, cream or paste. Preferred is a gel or semi-solid cream or paste.

What is claimed is:

1. A method for applying an electrolyte from a cup to a paddle for use on the skin of a patient, said cup being a flexible container having an open face, peripheral edges defining the open face, a layer of bonding agent disposed on said peripheral edges, and a protective cover positioned on said container to close off said open face and being removably secured to said layer of bonding agent, comprising the steps of providing an electrode paddle, providing said cup having a supply of electrolyte therein, removing said protective cover from said cup without removing said layer of bonding agent therefrom, pressing the open face of said cup against the surface of said electrode paddle to removably secure by said bonding agent said container having the electrolyte therein to the surface of said electrode paddle, and when said paddle is ready for use, removing said container from said paddle while squeezing said container to thereby dispense the electrolyte contents thereof onto said paddle, whereby said paddle may then be urged against the skin of a patient until firm and secure contact is made between the paddle and the skin of the patient.

2. The method in accordance with claim 1, including the step of distributing the electrolyte over the surface of the paddle, after said cup is removed therefrom.

* * * * *